(12) United States Patent
Yang

(10) Patent No.: US 8,154,725 B2
(45) Date of Patent: Apr. 10, 2012

(54) LINE SCANNING MEASUREMENT SYSTEM

(75) Inventor: Fu Shiang Yang, Sinpu Township, Hsinchu County (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 346 days.

(21) Appl. No.: 12/622,946

(22) Filed: Nov. 20, 2009

(65) Prior Publication Data

US 2011/0058169 A1 Mar. 10, 2011

(30) Foreign Application Priority Data

Sep. 10, 2009 (TW) .............................. 98130482 A

(51) Int. Cl.
*G01J 4/00* (2006.01)

(52) U.S. Cl. ....................................................... 356/364

(58) Field of Classification Search .................. 356/364, 356/367; 250/559.09
See application file for complete search history.

(56) References Cited

U.S. PATENT DOCUMENTS

| 7,202,950 | B2 | 4/2007 | Shribak et al. |
| 7,251,029 | B2 | 7/2007 | Kishikawa et al. |
| 7,286,226 | B2 | 10/2007 | Takeuchi et al. |
| 7,813,013 | B2 * | 10/2010 | Kain .............................. 358/474 |

* cited by examiner

*Primary Examiner* — Roy M Punnoose
(74) *Attorney, Agent, or Firm* — Egbert Law Offices PLLC

(57) ABSTRACT

A line scanning measurement system includes an illumination apparatus, a support, a telecentric optical element and a processor. The illumination apparatus is utilized for providing an extended polarized light beam. The support is utilized for mounting a sample, and the extended polarized light beam is directed at the sample. The telecentric optical element is utilized for directing a measurement light beam that has interacted with the sample toward a line scanning detector. The processor is utilized for obtaining the characteristic information of the sample in accordance with the signal measured by the line scanning detector.

24 Claims, 4 Drawing Sheets

LINE SCANNING MEASUREMENT SYSTEM

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The disclosure relates to a line scanning measurement system.

2. Description of Related Art Including Information Disclosed Under 37 CFR 1.97 and 37 CFR 1.98.

In modern optical technology, birefringence crystals such as waveplates, birefringence prisms, and liquid crystals are important optical components. In general, optical parameters of birefringence crystals such as principal axis, phase retardation/phase difference, refractive index, polarization characteristic and thickness play an important role in optical and biomedical industries. Therefore, it is absolutely important for practical applications and yield rates of optical elements to measure optical parameters accurately.

In the past, measuring systems were often based on single-point detection. Capturing full-field information of a sample requires measuring the sample repeatedly, taking a long time. U.S. Pat. No. 5,521,705 discloses a method for determining polarization properties. A pair of variable retarders is positioned in an optical path with their slow optical axes at a 45° angle to each other. A polarized light analyzer is also placed in the optical path between light retarders and a detector. The method determines the polarization properties of light from the intensities measured at different retardance levels.

U.S. Pat. No. 7,202,950 discloses a method for measuring retardance. A sample is illuminated by circularly polarized monochromatic light which is then analyzed by an elliptical analyzer at different settings. In addition, light conditioned by an elliptical polarizer at various settings illuminates a sample and the beam exiting the sample is analyzed by a circular analyzer.

However, the above-mentioned methods take a long time to measure a sample and set polarization parameters of polarizers repeatedly. Thus, finding a method to build a measurement system which measures characteristic parameters of a large-area sample rapidly is an important issue for the related industries.

BRIEF SUMMARY OF THE INVENTION

According to one exemplary embodiment, a line scanning measurement system comprises an illumination apparatus, a support, a telecentric optical element and a processor. The illumination apparatus is utilized for providing an extended polarized light beam. The support is utilized for mounting a sample, wherein the extended polarized light beam is directed at the sample. The telecentric optical element is utilized for directing a measurement light beam that has interacted with the sample toward a line scanning detector. The processor is utilized for controlling the support to move the sample or for controlling moving directions of the illumination apparatus, the telecentric optical element and the line scanning detector, and for obtaining characteristic information of the sample in accordance with the signal measured by the line scanning detector.

According to another exemplary embodiment, a line scanning measurement system comprises a plurality of illumination apparatuses, a support, a plurality of telecentric optical elements and a processor. The plurality of illumination apparatuses are utilized for providing a plurality of extended polarized light beams. The support is utilized for mounting a sample, wherein the plurality of extended polarized light beams are directed at the sample. The plurality of telecentric optical elements are utilized for directing a plurality of measurement light beams that have interacted with the sample toward a plurality of line scanning detectors. The processor is utilized for controlling the support to move the sample, or is utilized for controlling moving directions of the plurality of illumination apparatuses, the plurality of telecentric optical elements and the plurality of line scanning detectors; in addition, the process is also utilized for obtaining characteristic information of the sample in accordance with the signals measured by the plurality of line scanning detectors.

BRIEF DESCRIPTION OF THE SEVERAL VIEWS OF THE DRAWINGS

The accompanying drawings, which are incorporated in and constitute a part of this specification, illustrate embodiments of the disclosure and, together with the description, serve to explain the principles of the invention.

DETAILED DESCRIPTION OF THE INVENTION

Figure 1:
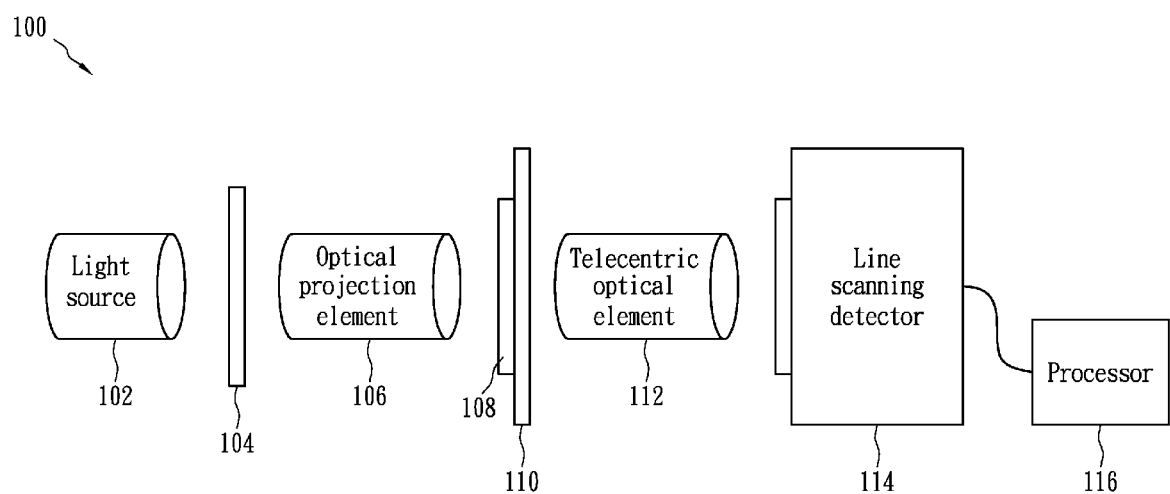
FIG. 1 shows a schematic view of a line scanning measurement system in accordance with an exemplary embodiment.

FIG. 1 shows a diagram of a line scanning measurement system in accordance with an exemplary embodiment. The line scanning measurement system 100 comprises a light source 102, a polarization element 104, an optical projection element 106, a sample 108, a support 110, a telecentric optical element 112, a line scanning detector 114 and a processor 116. The light source is utilized for providing an incident light beam, wherein the incident light beam can be set to be a visible light beam, an ultraviolet light beam or an infrared beam. The polarization element 104 is utilized for converting the incident light beam to a polarized light beam, wherein the polarization element 104 can be a circular polarizer, an elliptical polarizer or a linear polarizer, and the polarized light beam can be a right circularly polarized light beam, a left circularly polarized light beam, a right elliptically polarized light beam, a left elliptically polarized light beam or a linearly polarized light beam. The optical projection element 106 is utilized for extending a sectional area of the polarized light beam to provide an extended polarized light beam. The optical projection element 106 can be a lens set or a reflective imaging lens set. The telecentric optical element 112 can be a lens set or a reflective imaging lens set.

The support 110 is utilized for mounting the sample 108, wherein the extended polarized light beam is directed at the sample 108. The telecentric optical element 112 is utilized for directing a measurement light beam that has interacted with the sample 108 toward the line scanning detector 114. The processor 116 is utilized for obtaining characteristic information of the sample 108 in accordance with the signals measured by the line scanning detector 114, wherein the characteristic information is, for example, a phase retardation.

In accordance with another exemplary embodiment of a line scanning measurement system, the polarization element 104 is utilized for converting an incident light beam to a left circularly polarized light beam. The optical projection element 106 is utilized for extending a sectional area of the left circularly polarized light beam to provide an extended left circularly polarized light beam and directing the extended left circularly polarized light beam at the sample 108. In the exemplary embodiment, the telecentric optical element 112 is an object-side telecentric optical element. The line scanning detector 114 includes a plurality of linearly analyzers, wherein transmission axis directions of the plurality of linearly analyzers are different, the same or partially the same.

In accordance with another exemplary embodiment of a line scanning measurement system, the polarization element 104 is utilized for converting an incident light beam to a right circularly polarized light beam. The optical projection element 106 is utilized for extending a sectional area of the right circularly polarized light beam to provide an extended right circularly polarized light beam and directing the extended right circularly polarized light beam at the sample 108. In the exemplary embodiment, the telecentric optical element 112 is a double-sided telecentric optical element. The line scanning detector 114 includes a plurality of linearly analyzers and a plurality of retarders with different retardations, wherein transmission axis directions of the plurality of linearly analyzers are different, the same or partially the same.

Figure 2:
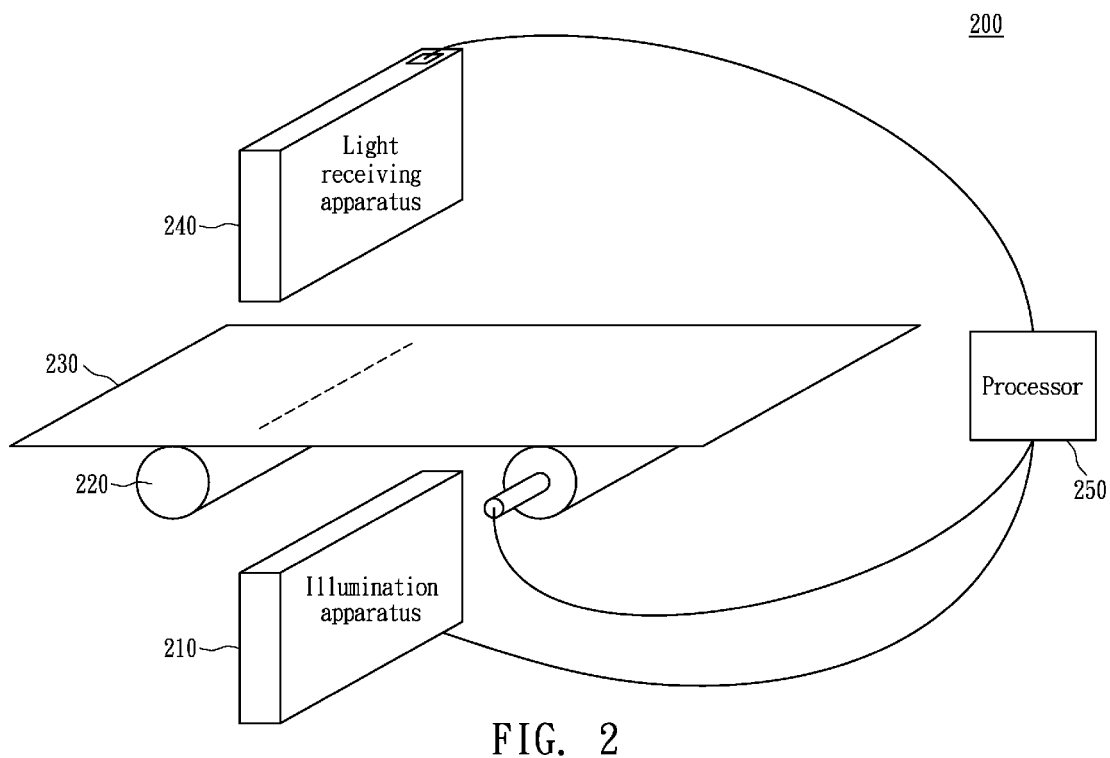
FIG. 2 shows a schematic view of a line scanning measurement system in accordance with another exemplary embodiment.

FIG. 2 shows a diagram of a line scanning measurement system in accordance with another exemplary embodiment. The line scanning measurement system 200 comprises an illumination apparatus 210, a support 220, a sample 230, a light receiving apparatus 240 and a processor 250. The illumination apparatus 210 is utilized for providing an extended polarized light beam which is directed at the sample 230. The illumination apparatus 210 comprises a light source, a polarization element and an optical projection element. The light source is utilized for providing an incident light beam, wherein the incident light beam can be a visible light beam, an ultraviolet light beam or an infrared beam. The polarization element is utilized for converting the incident light beam to a polarized light beam, wherein the polarization element can be a circular polarizer, an elliptical polarizer or a linear polarizer. The polarized light beam can be a right circularly polarized light beam, a left circularly polarized light beam, a right elliptically polarized light beam, a left elliptically polarized light beam or a linearly polarized light beam. The optical projection element is utilized for extending a sectional area of the polarized light beam to provide the extended polarized light beam. The optical projection element can be a lens set or a reflective imaging lens set. The support 220 is utilized for mounting the sample 230. The light receiving apparatus 240 is utilized for receiving a measurement light beam that has interacted with the sample 230. The light receiving apparatus 240 comprises a telecentric optical element and a line scanning detector, wherein the telecentric optical element can be a lens set or a reflective imaging lens set. The processor 250 is utilized for controlling the support 220 to move the sample 230, or is utilized for controlling moving directions of the illumination apparatus 210 and the light receiving apparatus 240; in addition, the processor 250 is also utilized for obtaining a phase retardation of the sample 230 and a direction of a principal axis of the sample 230 in accordance with signals measured by the light receiving apparatus 240.

Figure 3A:
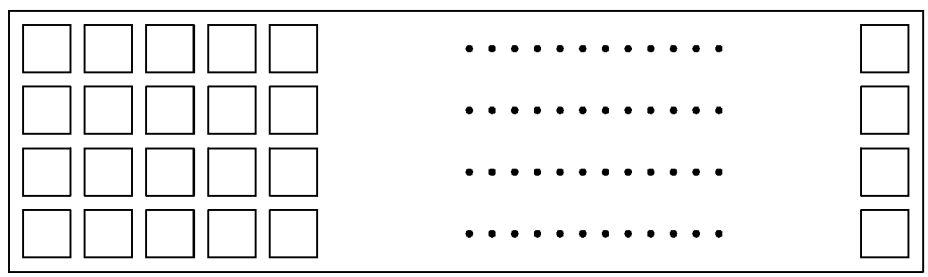
FIG. 3A illustrates a schematic view of an arrangement of sensing units of a four-line scanning detector in accordance with an exemplary embodiment.
Figure 3B:
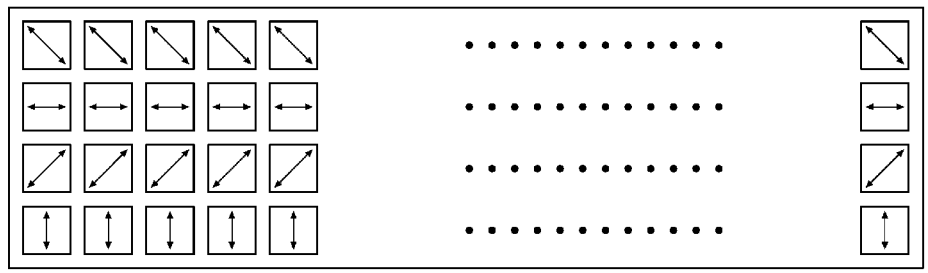
FIG. 3B illustrates a schematic view of an arrangement of linearly analyzers of a four-line scanning detector.

In accordance with another exemplary embodiment, the illumination apparatus 210 is utilized for providing an extended left circularly polarized light beam which is directed at the sample 230. In the exemplary embodiment, the light receiving apparatus 240 employs an object-side telecentric optical element. The line scanning detector in the light receiving apparatus 240 includes a plurality of linearly analyzers, wherein transmission axis directions of the plurality of linearly analyzers are, for example, 135°, 0°, 45° and 90°. FIG. 3A illustrates a diagram of an arrangement of sensing units of a four-line scanning detector in accordance with the exemplary embodiment. FIG. 3B illustrates a diagram of an arrangement of linearly analyzers of a four-line scanning detector which has four different transmission axis directions (the transmission axis directions of the linearly analyzers of each line are the same). The processor 250 is utilized for controlling the support 220 to move the sample 230 and for obtaining a phase retardation and a direction of a principal axis of the sample 230 in accordance with signals measured by the light receiving apparatus 240.

In accordance with another exemplary embodiment, the illumination apparatus 210 is utilized for providing an extended right circularly polarized light beam which is directed at the sample 230. In the exemplary embodiment, the light receiving apparatus 240 employs a double-sided telecentric optical element. The line scanning detector in the light receiving apparatus 240 includes a plurality of linearly analyzers and a plurality of retarders with different retardations, wherein transmission axis directions of the plurality of linearly analyzers are different, the same or partially the same.

In accordance with another exemplary embodiment of a line scanning measurement system, the system comprises a plurality of light sources, a plurality of polarization elements, a plurality of optical projection elements, a support, a plurality of telecentric optical elements and a processor. The plurality of light sources is utilized for providing a plurality of incident light beams, wherein the plurality of incident light beams can be visible light beams, ultraviolet light beams or infrared beams. The plurality of polarization elements is utilized for converting the plurality of incident light beams to a plurality of polarized light beams. The plurality of polarization elements are, for example, circular polarizers, elliptical polarizers or linear polarizers. The plurality of polarization elements can also comprise at least one circular polarizer and at least one elliptical polarizer; at least one circular polarizer and at least one linear polarizer; at least one elliptical polarizer and at least one linear polarizer; or at least one circular polarizer, at least one elliptical polarizer and at least one linear polarizer at the same time. The plurality of polarized light beams are right circularly polarized light beams, left circularly polarized light beams, right elliptically polarized light beams, left elliptically polarized light beams or linearly polarized light beams. The plurality of polarized light beams can also comprise at least one right circularly polarized light beam; at least one left circularly polarized light beam; at least one right elliptically polarized light beam; at least one left elliptically polarized light beam; or at least one linearly polarized light beam. The plurality of optical projection elements is utilized for extending sectional areas of the plurality of polarized light beams to provide the plurality of extended polarized light beams. The plurality of optical projection elements can be lens sets or reflective imaging lens sets. The plurality of telecentric optical elements can be lens sets or reflective imaging lens sets. The support is utilized for mounting a sample, wherein the plurality of extended polarized light beams are directed at the sample. The plurality of telecentric optical elements are utilized for directing a plurality of measurement light beams that have interacted with the sample toward a plurality of line scanning detectors. The processor is utilized for obtaining characteristic information of the sample in accordance with the signals measured by the plurality of line scanning detectors, wherein the characteristic information is, for example, a phase retardation.

Figure 4:
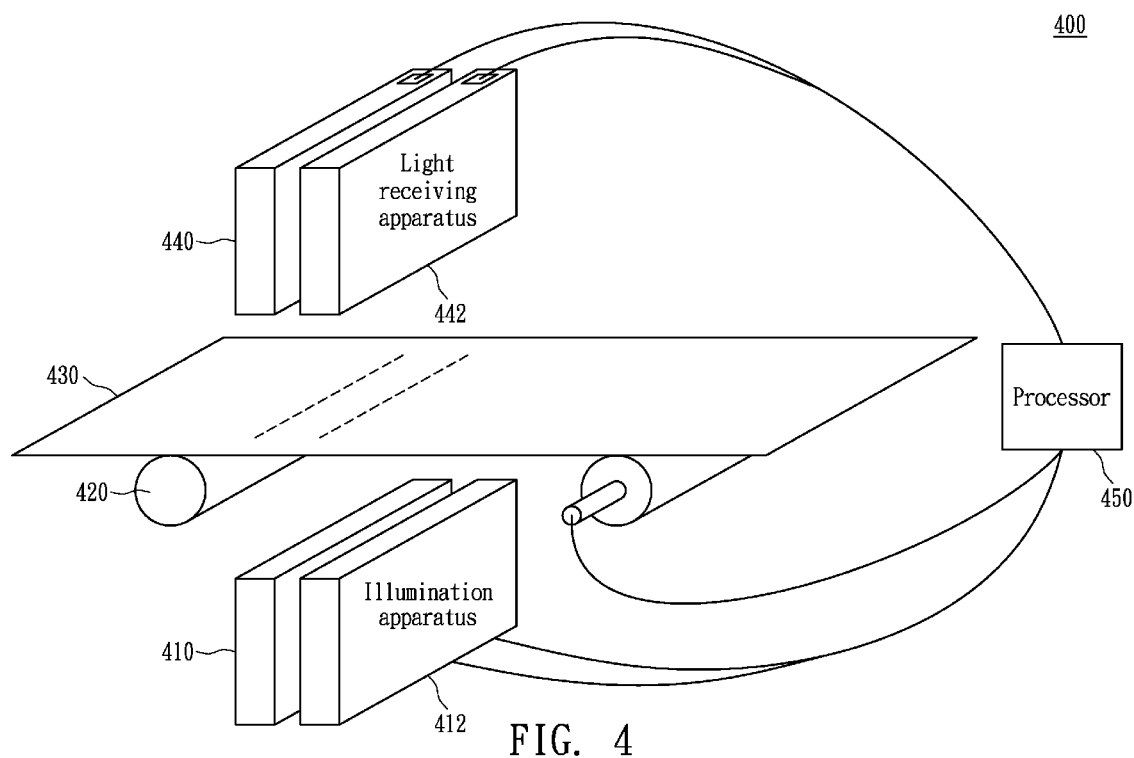
FIG. 4 shows a schematic view of a line scanning measurement system in accordance with another exemplary embodiment.

FIG. 4 shows a diagram of a line scanning measurement system in accordance with another exemplary embodiment. The line scanning measurement system 400 comprises illumination apparatuses 410 and 412, a support 420, a sample 430, light receiving apparatuses 440 and 442, and a processor 450. The illumination apparatuses 410 and 412 are utilized for providing extended polarized light beams which are directed at the sample 430. The illumination apparatus 410 or the illumination apparatus 412 comprises a light source, a polarization element and an optical projection element. The light source is utilized for providing an incident light beam, wherein the incident light beam can be a visible light beam, an ultraviolet light beam or an infrared beam. The polarization element is utilized for converting the incident light beam to a polarized light beam. In accordance with the exemplary embodiment, polarization elements used in the illumination apparatuses 410 and 412 are circular polarizers which are utilized for providing a right circularly polarized light beam and a left circularly polarized light beam, respectively. Subsequently, optical projection elements in the illumination apparatuses 410 and 412 are utilized for extending a sectional area of the right circularly polarized light beam and a sectional area of the left circularly polarized light beam, respectively, to provide an extended right circularly polarized light beam and an extended left circularly polarized light beam. The support 420 is utilized for mounting the sample 430. The light receiving apparatuses 440 and 442 are utilized for receiving measurement light beams that have interacted with the sample 430.

In accordance with an exemplary embodiment of the disclosure, the light receiving apparatus 440 or the light receiving apparatus 442 comprises an object-side telecentric optical element and a line scanning detector with a plurality of linearly analyzers, wherein transmission axis directions of the plurality of linearly analyzers are different, the same or partially the same. The processor 450 is utilized for controlling the support 420 to move the sample 430 or for controlling moving directions of the illumination apparatuses 410 and 412 and the light receiving apparatuses 440 and 442, and for obtaining a phase retardation of the sample 430 and a direction of a principal axis of the sample 430 in accordance with signals measured by the light receiving apparatuses 440 and 442.

In accordance with another exemplary embodiment of a line scanning measurement system, polarization elements used in the illumination apparatuses 410 and 412 are elliptical polarizers which are utilized for providing a right elliptically polarized light beam and a left elliptically polarized light beam, respectively. Subsequently, optical projection elements in the illumination apparatuses 410 and 412 are utilized for extending a sectional area of the right elliptically polarized light beam and a sectional area of the left elliptically polarized light beam, respectively, to provide an extended right elliptically polarized light beam and an extended left elliptically polarized light beam. The light receiving apparatus 440 or the light receiving apparatus 442 employs a double-sided telecentric optical element and a line scanning detector with a plurality of linearly analyzers and a plurality of retarders with different retardations, wherein transmission axis directions of the plurality of linearly analyzers are different, the same or partially the same.

In summary, this disclosure discloses a system utilizing a telecentric optical element and a line scanning detector, wherein the system is compatible with former related algorithms. In addition, the system measures characteristic parameters of a large-area sample rapidly.

The above-described exemplary embodiments are intended to be illustrative of the invention principle only. Those skilled in the art may devise numerous alternative embodiments without departing from the scope of the following claims.

I claim:

1. A line scanning measurement system, comprising:
   an illumination apparatus utilized for providing an extended polarized light beam;
   a support utilized for mounting a sample, wherein the extended polarized light beam is directed at the sample;
   a telecentric optical element utilized for directing a measurement light beam that has interacted with the sample toward a line scanning detector; and
   a processor utilized for controlling the support to move the sample, or utilized for controlling moving directions of the illumination apparatus, the telecentric optical element and the line scanning detector; wherein said processor is also utilized for obtaining characteristic information of the sample in accordance with the signals measured by the line scanning detector, wherein the characteristic information includes at least one phase retardation or at least one direction of a principal axis.

2. The system of claim 1, wherein the illumination apparatus comprises:
   a polarization element utilized for converting an incident light beam to a polarized light beam, wherein the incident light beam is a visible light beam, an ultraviolet light beam or an infrared beam; and
   an optical projection element utilized for extending a sectional area of the polarized light beam to provide the extended polarized light beam.

3. The system of claim 2, wherein the illumination apparatus further comprises a light source utilized for providing the incident light beam.

4. The system of claim 2, wherein the polarization element is a circular polarizer, an elliptical polarizer or a linear polarizer.

5. The system of claim 2, wherein the polarized light beam is a right circularly polarized light beam, a left circularly polarized light beam, a right elliptically polarized light beam, a left elliptically polarized light beam or a linearly polarized light beam.

6. The system of claim 1, wherein the telecentric optical element is an object-side telecentric optical element and the line scanning detector includes a plurality of linearly analyzers.

7. The system of claim 6, wherein transmission axis directions of the plurality of linearly analyzers are different, the same or partially the same.

8. The system of claim 1, wherein the telecentric optical element is a double-sided telecentric optical element and the line scanning detector includes a plurality of linearly analyzers and a plurality of retarders with different retardations.

9. The system of claim 8, wherein transmission axis directions of the plurality of linearly analyzers are different, the same or partially the same.

10. The system of claim 2, wherein the optical projection element is a lens set or a reflective imaging lens set.

11. The system of claim 1, wherein the telecentric optical element is a lens set or a reflective imaging lens set.

12. A line scanning measurement system, comprising:
   a plurality of illumination apparatuses utilized for providing a plurality of extended polarized light beams;
   a support utilized for mounting a sample, wherein the plurality of extended polarized light beams are directed at the sample;
   a plurality of telecentric optical elements utilized for directing a plurality of measurement light beams that have interacted with the sample toward a plurality of line scanning detectors; and
   a processor utilized for controlling the support to move the sample or utilized for controlling moving directions of the plurality of illumination apparatuses, the plurality of telecentric optical elements and the plurality of line scanning detectors; wherein said processor is also utilized for obtaining characteristic information of the sample in accordance with the signals measured by the plurality of line scanning detectors, wherein the characteristic information includes at least one phase retardation and or at least one direction of a principal axis.

13. The system of claim 12, wherein the plurality of illumination apparatuses comprise:
   a plurality of polarization elements utilized for converting a plurality of incident light beams to a plurality of polarized light beams, wherein the plurality of incident light beams are visible light beams, ultraviolet light beams or infrared beams; and
   a plurality of optical projection elements utilized for extending sectional areas of the plurality of polarized light beams to provide the plurality of extended polarized light beams.

14. The system of claim 13, wherein the plurality of illumination apparatuses further comprise a plurality of light sources utilized for providing the plurality of incident light beams.

15. The system of claim 13, wherein the plurality of polarization elements are circular polarizers, elliptical polarizers or linear polarizers.

16. The system of claim 13, wherein the plurality of polarization elements comprise at least one circular polarizer, at least one elliptical polarizer or at least one linear polarizer.

17. The system of claim 13, wherein the plurality of polarized light beams are right circularly polarized light beams, left circularly polarized light beams, right elliptically polarized light beams, left elliptically polarized light beams or linearly polarized light beams.

18. The system of claim 13, wherein the plurality of polarized light beams comprise at least one right circularly polarized light beam, at least one left circularly polarized light beam, at least one right elliptically polarized light beam, at least one left elliptically polarized light beam or at least one linearly polarized light beam.

19. The system of claim 12, wherein the plurality of telecentric optical elements are object-side telecentric optical elements and the plurality of line scanning detectors include a plurality of linearly analyzers.

20. The system of claim 19, wherein transmission axis directions of the plurality of linearly analyzers are different, the same or partially the same.

21. The system of claim 12, wherein the plurality of telecentric optical elements are double-sided telecentric optical elements and the plurality of line scanning detectors include a plurality of linearly analyzers and a plurality of retarders with different retardations.

22. The system of claim 21, wherein transmission axis directions of the plurality of linearly analyzers are different, the same or partially the same.

23. The system of claim 13, wherein the plurality of optical projection elements are lens sets or reflective imaging lens sets.

24. The system of claim 12, wherein the plurality of telecentric optical elements are lens sets or reflective imaging lens sets.

* * * * *